(12) United States Patent
Park et al.

(10) Patent No.: US 11,647,710 B2
(45) Date of Patent: May 16, 2023

(54) METHOD FOR PREPARATION OF SOYBEAN LEAF HAVING HIGH CONTENT OF ISOFLAVONE DERIVATIVE IN DARK CONDITION AND SOYBEAN LEAF HAVING HIGH CONTENT OF ISOFLAVONE DERIVATIVE PREPARED THEREBY

(71) Applicant: INDUSTRY-ACADEMIC COOPERATION FOUNDATION GYEONGSANG NATIONAL UNIVERSITY, Jinju-si (KR)

(72) Inventors: Ki Hun Park, Jinju-si (KR); Jeong Ho Kim, Jinju-si (KR); Yeong Jun Ban, Jinju-si (KR); Yeong Hun Song, Jinju-si (KR)

(73) Assignee: INDUSTRY-ACADEMIC COOPERATION FOUNDATION GYEONGSANG NATIONAL UNIVERSITY, Jinju-si (KR)

( * ) Notice: Subject to any disclaimer, the term of this patent is extended or adjusted under 35 U.S.C. 154(b) by 0 days.

(21) Appl. No.: 17/630,007

(22) PCT Filed: Jul. 24, 2020

(86) PCT No.: PCT/KR2020/009766
§ 371 (c)(1),
(2) Date: Jan. 25, 2022

(87) PCT Pub. No.: WO2021/015583
PCT Pub. Date: Jan. 28, 2021

(65) Prior Publication Data
US 2022/0256796 A1    Aug. 18, 2022

(30) Foreign Application Priority Data
Jul. 25, 2019 (KR) ........................ 10-2019-0090238

(51) Int. Cl.
| | | |
|---|---|---|
| *A01H 5/12* | (2018.01) | |
| *A23L 23/10* | (2016.01) | |
| *A23L 33/105* | (2016.01) | |
| *A23L 13/40* | (2023.01) | |
| *A61K 8/9789* | (2017.01) | |
| *A61P 9/00* | (2006.01) | |
| *A61P 19/10* | (2006.01) | |
| *A01H 6/54* | (2018.01) | |
| *A01H 3/02* | (2006.01) | |
| *A21D 2/36* | (2006.01) | |
| *A23F 3/14* | (2006.01) | |
| *A61K 31/352* | (2006.01) | |
| *A61K 36/48* | (2006.01) | |

(52) U.S. Cl.
CPC ................ *A01H 5/12* (2013.01); *A01H 3/02* (2013.01); *A01H 6/54* (2018.05); *A21D 2/362* (2013.01); *A23F 3/14* (2013.01); *A23L 13/428* (2016.08); *A23L 23/10* (2016.08); *A23L 33/105* (2016.08); *A61K 8/9789* (2017.08); *A61K 31/352* (2013.01); *A61K 36/48* (2013.01); *A61P 9/00* (2018.01); *A61P 19/10* (2018.01)

(58) Field of Classification Search
None
See application file for complete search history.

(56) References Cited

FOREIGN PATENT DOCUMENTS

| | | |
|---|---|---|
| CN | 106047889 A | 10/2016 |
| KR | 1020050104097 A | 11/2005 |
| KR | 101451298 B1 | 10/2014 |

OTHER PUBLICATIONS

Kong et al., Korean Journal of Pesticide Science, vol. 3 (1), issue, No. 3, 2018, 16 pages.*
Yuk et al., Journal of Agricultural and Food Chemistry, 2016, 64, pp. 7315-7324.*
Aguiar et al. (2014). Use of soy isoflavones on hormone replacement therapy during climacteric. African Journal of Pharmacy and Pharmacology, 8(42), 1071-1078.
Ban et al. (2020). Comparative investigation on metabolites changes in soybean leaves by ethylene and activation of collagen synthesis. Industrial Crops and Products, 154, 112743-1 to 112743-8.
Hudson (2001). Soy and women's health. Female Patient, 26(12), 26-37.
Kim et al. (2001). A Case of Inflammatory Pseudotumor of the Uterus. Korean Journal of Obstetrics and Gynecology, 14(2), 389-392.
Kirakosyan et al. (2006). Isoflavone levels in five soybean (Glycine max) genotypes are altered by phytochrome-mediated light treatments. Journal of agricultural and food chemistry, 54(1), 54-58.
Kong et al. (2018). Effect of postharvest treatment of ethylene of light on total flavonoid in soybean leaf. Korean J Pestic Sci, 22, 153-157.

(Continued)

*Primary Examiner* — Michael V Meller
(74) *Attorney, Agent, or Firm* — Caesar Rivise, PC

(57) ABSTRACT

The present invention relates to a method for preparation of soybean leaves having a high content of an isoflavone derivative in a dark condition and soybean leaves having a high content of an isoflavone derivative prepared thereby. Specifically, treatment of a soybean plant 20 days to 60 days after seeding with a predetermined concentration of ethylene in a dark condition was found to accumulate higher concentrations of isoflavone derivatives in soybean leaves than treatment with ethephon in a light condition, which requires a high level of energy. Therefore, when used, the method of the present invention can economically and quickly prepare soybean leaves having a very high content of isoflavones, and the soybean leaves having a high content of isoflavone derivatives, an extract of the soybean leaves, and a fraction of the extract can be advantageously used as a food and medicine material against diseases caused by estrogen unbalance and deficient antioxidant activity.

1 Claim, 9 Drawing Sheets

(56) References Cited

OTHER PUBLICATIONS

Kuiper et al. (1997). Comparison of the ligand binding specificity and transcript tissue distribution of estrogen receptors α and β. Endocrinology, 138(3), 863-870.
Setchell et al. (1999). Dietary isoflavones: biological effects and relevance to human health. The journal of nutrition, 129(3), 758S-767S.
Wilson et al. (1950). Acetylcholinesterase X. Mechanism of the catalysis of acylation reactions. Journal of Biological Chemistry, 186(2), 781-790.
Yuk et al. (2016). Ethylene induced a high accumulation of dietary isoflavones and expression of isoflavonoid biosynthetic genes in soybean (Glycine max) leaves. Journal of agricultural and food chemistry, 64(39), 7315-7324.
English language abstract for CN 106047889 A (2016).
English language abstract for KR 101451298 B1 (2014).
English language abstract for KR 1020050104097 A (2005).
International Search Report from corresponding PCT/KR2020/009766 dated Dec. 29, 2020.

* cited by examiner

METHOD FOR PREPARATION OF SOYBEAN LEAF HAVING HIGH CONTENT OF ISOFLAVONE DERIVATIVE IN DARK CONDITION AND SOYBEAN LEAF HAVING HIGH CONTENT OF ISOFLAVONE DERIVATIVE PREPARED THEREBY

CROSS-REFERENCE TO RELATED APPLICATIONS

This application is a U.S. national phase of PCT/KR2020/009766, filed Jul. 24, 2020, and claims priority to KR 10-2019-0090238, filed Jul. 25, 2019, the contents of which are incorporated herein by reference in their entireties for all purposes.

BACKGROUND OF THE INVENTION

1. Field of the Invention

The present invention relates to a method for preparation of soybean leaves having a high content of an isoflavone derivative in a dark condition, the soybean leaves having a high content of an isoflavone derivative prepared thereby, a use of the soybean leaves soybean leaves having a high content of an isoflavone derivative, and a method for mass production of isoflavone derivatives from the soybean leaves.

2. Description of the Related Art

Estrogen, a female hormone, starts to decrease after the age of 40, eventually causing menopause. When estrogen decreases, aging begins in the bones, heart, skin, and brain, which are the points of action of this hormone. In order to suppress the aging process, an estrogen substitute is desperately required, and an isoflavone derivative having structural similarity has been reported as an effective estrogen substitute.

An isoflavone derivative is a representative flavonoid with excellent pharmacological efficacy, and a lot of capital is being invested in the development of a functional plant having a high content of an isoflavone derivative worldwide. Isoflavone is nonsteroidal estrogen and is called phytoestrogen because its chemical and physiological properties are similar to those of estrogen. It is a substance that has estrogenic or anti-estrogenic action by competitively binding to the estrogen receptor (Hudson, 2001). Isoflavone is similar in structure to estrogen, a female hormone, and thus shows useful physiological activities of estrogen. Ingestion of isoflavone is known to regulate endocrine status in women and affect ovarian periodicity (Kenneth, Setchell, & Cassidy, 1999). In particular, isoflavone has been reported to reduce the risk of osteoporosis, one of the menopausal symptoms that may appear due to a lack of female hormones, and to lower the level of plasma cholesterol (Obstetrics & Gynecology 2001. 389). Isoflavone is also known to reduce the risk of coronary arterial heart disease (CAHD) and has excellent antioxidant activity.

Isoflavone derivatives exist in the form of glycosides in which sugars are linked by beta-glycosidic bonds or in the form of non-glycosides in which sugars are separated. Examples of non-glycoside include genistein, daidzein, and glycitein, and examples of glycoside include genistin, daidzin, and glycitin. Soybean-derived non-fermented foods contain many glycosides, whereas non-glycosides are mainly present in fermented foods such as soybean paste because sugars are decomposed from glycosides by fermentation-related bacteria.

Non-glycosides such as genistein and daidzein in soybeans have a high affinity for ER-beta (estrogen receptor beta), an estrogen receptor (ER), and thus they are the most effective estrogen substitutes (Endocrinology 1997, 863). As such, soybean isoflavone is a useful biological material as a substitute for estrogen, but there are difficulties in processing such as extraction, purification and commercialization of isoflavone derivatives due to the high content of proteins, fats and carbohydrates contained in soybeans.

Many studies are being conducted to develop soybeans with a high content of isoflavone. Recently, a cultivation method technique for producing soybean leaves having a high content of an isoflavone derivative by treating soybean leaves with ethylene or ethephon, an ethylene donor, has been reported. This is an effective technology that can produce soybean leaves in which isoflavone derivatives are accumulated more than 13,000 μg/ml in a wide field (Korean Patent No. 10-1451298). However, this technique has limitations in that it is possible only in an enclosed space, that consumers have a reluctance to the chemical ethephon, and that an LED artificial light that requires a high level of energy is absolutely necessary.

The photosynthetic process of plants is divided into a light reaction and a dark reaction. In the dark reaction, metabolites are synthesized by Calvin Benison cycle (J. Biol. Chem. 1950, 781). The present inventors have been studying a technique for cultivating soybean leaves having a high content of an isoflavone derivative in a dark condition that does not require energy. In the course of the study, the present inventors found that it is possible to synthesize secondary metabolites including carbohydrates, which are primary metabolites, by using ATP and NADPH obtained in a light reaction in a dark condition.

Accordingly, the present inventors have completed the present invention by revealing that soybean leaves containing a high content of isoflavones can be produced with higher efficiency by treating soybean leaves with a high concentration of ethylene in a closed space even in a dark condition.

SUMMARY OF THE INVENTION

It is an object of the present invention to provide a method for preparation of soybean leaves having a high content of an isoflavone derivative, comprising a step of treating soybean leaves with ethylene in a dark condition.

It is another object of the present invention to provide the soybean leaves having a high content of an isoflavone derivative prepared by the above method.

It is another object of the present invention to provide a use of a food and medicine material comprising the soybean leaves having a high content of an isoflavone derivative, an extract of the soybean leaves, or a fraction of the extract.

It is another object of the present invention to provide a method for mass production of isoflavone derivatives from soybean leaves using ethylene in a dark condition.

To achieve the above objects, the present invention provides a method for preparation of soybean leaves having a high content of an isoflavone derivative represented by [Formula 1] below, comprising a step of treating soybean leaves with ethylene in a dark condition;

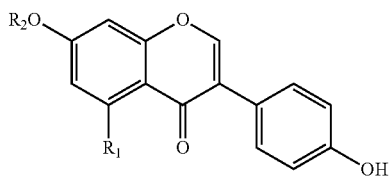

[Formula 1]

(In formula 1, $R_1$ is independently H or OH, and $R_2$ is independently glucose or glucose malonate.)

The present invention also provides the soybean leaves having a high content of an isoflavone derivative prepared by the above method.

The present invention also provides a composition comprising the soybean leaves having a high content of an isoflavone derivative according to the present invention, an extract of the soybean leaves, or a fraction of the extract.

The present invention also provides a pharmaceutical composition comprising the soybean leaves having a high content of an isoflavone derivative according to the present invention, an extract of the soybean leaves, or a fraction of the extract as an active ingredient for the prevention and treatment of a disease caused by estrogen deficiency.

The present invention also provides a health functional food comprising the soybean leaves having a high content of an isoflavone derivative according to the present invention, an extract of the soybean leaves, or a fraction of the extract as an active ingredient for the prevention and amelioration of a disease caused by estrogen deficiency.

The present invention also provides a pharmaceutical composition for antioxidant, comprising the soybean leaves having a high content of an isoflavone derivative according to the present invention, an extract of the soybean leaves, or a fraction of the extract as an active ingredient.

The present invention also provides a health functional food for antioxidant, comprising the soybean leaves having a high content of an isoflavone derivative according to the present invention, an extract of the soybean leaves, or a fraction of the extract as an active ingredient.

The present invention also provides a pharmaceutical composition for skin care, comprising the soybean leaves having a high content of an isoflavone derivative according to the present invention, an extract of the soybean leaves, or a fraction of the extract as an active ingredient.

The present invention also provides a cosmetic composition for skin care, comprising the soybean leaves having a high content of an isoflavone derivative according to the present invention, an extract of the soybean leaves, or a fraction of the extract as an active ingredient.

The present invention also provides a health functional food for skin care, comprising the soybean leaves having a high content of an isoflavone derivative according to the present invention, an extract of the soybean leaves, or a fraction of the extract as an active ingredient.

The present invention also provides a tea using the soybean leaves having a high content of an isoflavone derivative according to the present invention.

The present invention also provides a method for producing a tea using the soybean leaves having a high content of an isoflavone derivative according to the present invention.

The present invention also provides a method for mass production of isoflavone derivatives from soybean leaves using ethylene.

In addition, the present invention provides a method for mass production of isoflavone derivatives comprising the following steps:

1) preparing soybean leaves by treating soybean leaves with ethylene in a dark condition; and 2) isolating isoflavone derivatives by extracting the soybean leaves of step 1) above.

ADVANTAGEOUS EFFECT

In the present invention, treatment of a soybean plant 20 days to 60 days after seeding with a predetermined concentration of ethylene in a dark condition was found to accumulate higher concentrations of isoflavone derivatives in soybean leaves than treatment with ethephon in a light condition, which requires a high level of energy. Therefore, when used, the method of the present invention can economically and quickly prepare soybean leaves having a very high content of isoflavones, and the soybean leaves having a high content of isoflavone derivatives, an extract of the soybean leaves, and a fraction of the extract can be advantageously used as a food and medicine material against diseases caused by estrogen unbalance and deficient antioxidant activity.

DESCRIPTION OF THE PREFERRED EMBODIMENTS

Hereinafter, the present invention is described in detail.

The present invention provides a method for preparation of soybean leaves having a high content of an isoflavone derivative, comprising a step of treating soybean leaves with ethylene in a dark condition.

The ethylene treatment in a dark condition may be carried out in a closed space completely blocked from light.

The temperature of the closed space is preferably 20° C. to 40° C., and more preferably 25° C. to 35° C., but not always limited thereto.

The humidity of the closed space is preferably 50% to 80%, and more preferably 60% to 70%, but not always limited thereto.

The soybean leaves are preferably soybean leaves days or more after seeding, and more preferably soybean leaves 50 days after seeding, but not always limited thereto.

The ethylene is the simplest olefinic hydrocarbon (chemical formula: $C_2H_4$) and is a colorless, sweet gas. As a kind of plant hormone, it has the effect of accelerating the maturation of plant tissues such as physiological changes after harvest of fruits and vegetables, especially the maturation of horticultural crops or yellowing of leafy vegetables.

The ethylene is preferably treated at a concentration of 500 to 4000 ppm, and more preferably at a concentration of 2500 to 3500 ppm, but not always limited thereto.

The ethylene is preferably treated for 6 hours to 72 hours, and more preferably for 6 hours to 48 hours, but not always limited thereto.

The ethylene can be treated before or after harvesting soybean leaves, and preferably, it is possible to treat before harvesting soybean leaves, but not always limited thereto.

The isoflavone derivative is preferably a compound represented by the following [Formula 1], and more preferably any one of the compounds represented by the following [Formula 2] to [Formula 5], but not always limited thereto.

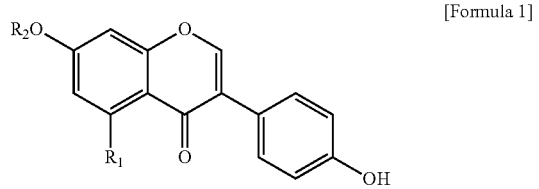

[Formula 1]

(In formula 1, $R_1$ is independently H or OH, and $R_2$ is independently glucose or glucose malonate.)

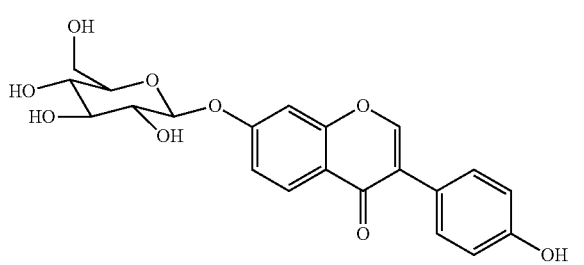

[Formula 2]

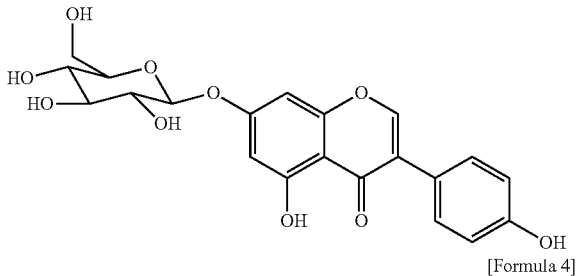

[Formula 3]

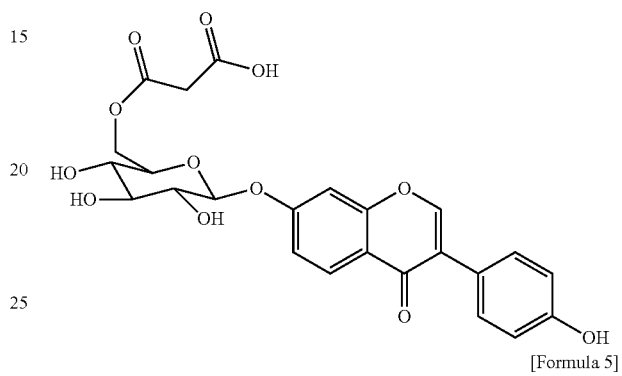

[Formula 4]

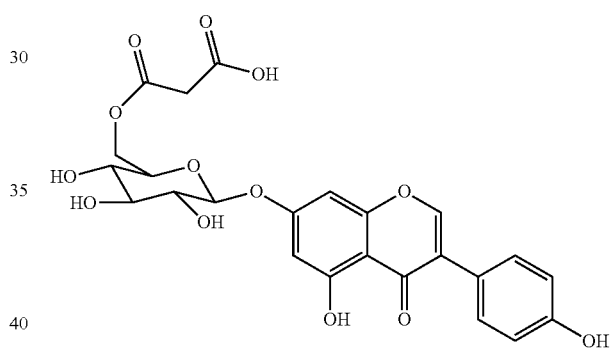

[Formula 5]

The present invention also provides the soybean leaves having a high content of an isoflavone derivative prepared by the above method.

The isoflavone derivative is preferably a compound represented by [Formula 1], and more preferably any one of the compounds represented by [Formula 2] to [Formula 5], but not always limited thereto.

Figure 1:
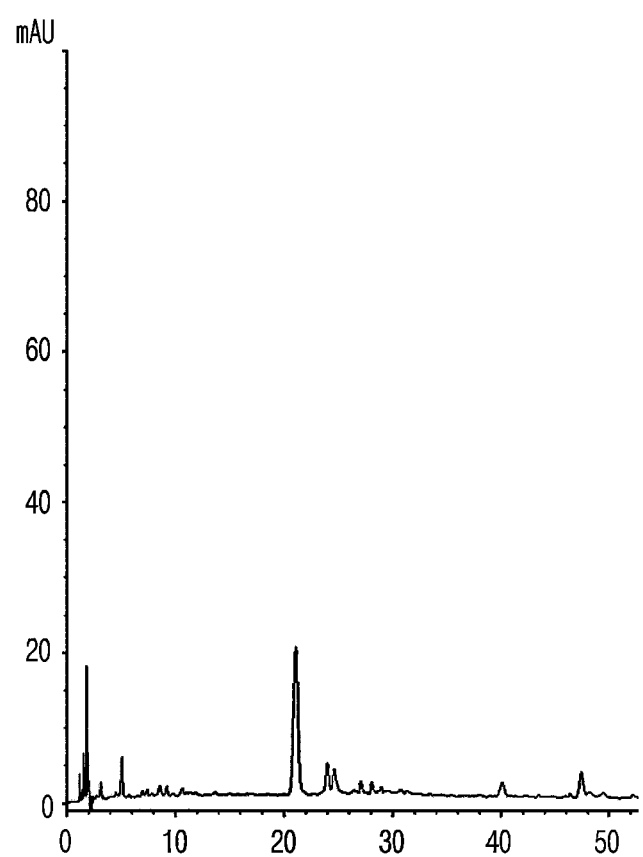
FIG. 1 is a graph showing the HPLC chromatogram of the ethanol extract of soybean leaves not treated with ethylene.

In a specific embodiment of the present invention, the present inventors treated a soybean plant 20 days to 60 days after seeding with ethylene in a dark condition. As a result, it was confirmed that the isoflavone derivative significantly increased in soybean leaves after the treatment than before the treatment (see FIGS. 1 to 3). In addition, it was confirmed that isoflavone derivatives were not detected in soybean leaves that were not treated with ethylene.

In soybean leaves treated with ethylene in a dark condition, it was confirmed that four isoflavone derivatives, daidzin, genistin, malonyl daidzin, and malonyl genistin were rapidly accumulated in the soybean leaves (see Tables 5 and 6). In addition, soybean leaves treated with ethylene in a dark condition were extracted with ethanol to obtain an extract, which was separated and purified to obtain four isoflavone derivatives, daidzin, genistin, malonyl daidzin and malonyl genistin (see FIGS. 4 to 8).

In addition, the present inventors performed quantitative analysis on four isoflavone derivatives, daidzin, genistin, malonyl daidzin and malonyl genistin, isolated from soybean leaves harvested after ethylene treatment in a dark condition. As a result, it was confirmed that the content of isoflavone derivatives was significantly increased in soybean leaves harvested after ethylene treatment in a dark condition compared to soybean leaves treated with ethephon. Therefore, it was confirmed that the method of harvesting soybean leaves after ethylene treatment in a dark condition is possible as a method for preparation of soybean leaves having a high content of an isoflavone derivative (see Table 7 and FIG. 9).

The present invention also provides a method for mass production of isoflavone derivatives from soybean leaves using ethylene in a dark condition.

Specifically, the method is preferably performed by a method comprising the following steps:

1) preparing soybean leaves by treating soybean leaves with ethylene in a dark condition; and 2) isolating isoflavone derivatives by extracting the soybean leaves of step 1) above.

In the method, the soybean leaves of step 1) are preferably soybean leaves 20 days or more after seeding, more preferably soybean leaves 50 days after seeding, and most preferably soybean leaves 20 to 60 days after seeding.

In the method, the ethylene of step 1) can be treated before or after harvesting soybean leaves.

In the method, the ethylene of step 1) is preferably treated at a concentration of 500 to 4000 ppm, and more preferably at a concentration of 2500 to 3500 ppm.

In the method, the isoflavone derivative is preferably a compound represented by [Formula 1], and more preferably any one of the compounds represented by [Formula 2] to [Formula 5].

In the present invention, soybean leaves having a high content of an isoflavone derivative are prepared by treating soybean leaves with ethylene in a dark condition, and the preparation method can be effectively used as a method for mass production of isoflavone derivatives.

The present invention also provides a composition comprising the soybean leaves having a high content of an isoflavone derivative prepared by treating with ethylene in a dark condition, an extract of the soybean leaves, or a fraction of the extract.

The extract of soybean leaves or the fraction thereof is preferably prepared by a preparation method comprising the following steps, but not always limited thereto:

1) extracting soybean leaves by adding an extraction solvent;

2) filtering the extract of step 1);

3) concentrating the filtered extract of step 2) under reduced pressure and drying thereof to prepare an extract of soybean leaves; and 4) preparing a fraction of soybean leaves by additionally extracting the extract of soybean leaves of step 3) with an organic solvent.

In the method, the soybean leaves of step 1) are collected from soybean plants in which isoflavones are highly accumulated after treating with ethylene in a dark condition. The ethylene treatment is possible even after harvesting the plant, but it is more preferable to treat it before harvesting. Both the leaves or roots of the soybean plant treated with ethylene are available, and according to a preferred embodiment of the present invention, it is preferable to use soybean leaves, but not always limited thereto.

In the method, it is preferable to use water, alcohol, or a mixture thereof as the extraction solvent of step 1). It is preferable to use a C1 to C2 lower alcohol as the alcohol, and it is preferable to use ethanol or methanol as the lower alcohol. As the extraction method, it is preferable to use shaking extraction, Soxhlet extraction or reflux extraction, but not always limited thereto. It is preferable to extract by adding the extraction solvent in an amount of 1 to 10 times the amount of dried soybean leaves, and it is more preferable to extract by adding in an amount of 4 to 6 times. The extraction temperature is preferably 20° C. to 100° C., and more preferably 20° C. to 40° C., but not always limited thereto. In addition, the extraction time is preferably 10 to 48 hours, more preferably 15 to 30 hours, and most preferably 24 hours, but not always limited thereto. The number of extractions is preferably 1 to 5 times, more preferably 3 to 4 times, and most preferably 3 times, but not always limited thereto.

In the method, the concentration under reduced pressure in step 3) is preferably performed by using a vacuum concentrator or a vacuum rotary evaporator, but not always limited thereto. Drying is preferably performed by reduced-pressurized drying, vacuum drying, boiling drying, spray drying, or freeze drying, but not always limited thereto.

In the method, as the extract of soybean leaves in step 4), it is preferable to use a dark brown crude extract, which is an extract of soybean leaves concentrated under reduced pressure, but not always limited thereto. In addition, the organic solvent is preferably n-hexane, chloroform, ethyl acetate or butanol, and more preferably chloroform according to a preferred embodiment of the present invention, but not always limited thereto. The fraction is preferably an n-hexane fraction, a chloroform fraction, an ethyl acetate fraction, a butanol fraction or a water fraction obtained by suspending the extract of soybean leaves in water and then sequentially fractionating thereof with n-hexane, chloroform, ethyl acetate, butanol and water, but not always limited thereto. The fraction can be obtained by repeating the fractionation process 1 to 5 times, preferably 3 times from the extract of soybean leaves, and it is preferable to concentrate under reduced pressure after the fractionation, but not always limited thereto.

The present invention also provides a pharmaceutical composition comprising the soybean leaves having a high content of an isoflavone derivative prepared by treating with ethylene in a dark condition, an extract of the soybean leaves, or a fraction of the extract as an active ingredient for the prevention and treatment of a disease caused by estrogen deficiency.

The disease caused by estrogen deficiency is preferably any one disease selected from the group consisting of osteoporosis, heart disease, breast cancer, vulvar disease, hyperlipidemia, skin aging, and hot flushes, but not always limited thereto.

The physiological activity of the isoflavone derivatives isolated from the soybean leaves having a high content of isoflavones of the present invention has been well established. Therefore, the extract of soybean leaves and its fractions containing the above compounds can be effectively used as a pharmaceutical composition for the prevention and treatment of a disease caused by estrogen deficiency.

The composition of the present invention can further include suitable carriers, excipients and diluents generally used in the preparation of pharmaceutical compositions.

The composition of the present invention can be administered by orally or parenterally and the parenteral administration includes intraperitoneal injection, intrarectal injection, subcutaneous injection, intravenous injection, intramuscular injection or intrathoracic injection, but not always limited thereto.

The composition of the present invention can be formulated and used in the form of oral formulations such as powders, granules, tablets, capsules, suspensions, emulsions, syrups and aerosols; external preparations; suppositories and sterile injection solutions, suppositories, and sterile injection solutions according to the conventional method, respectively. The carriers, excipients and diluents that can be included in the composition of the present invention are exemplified by lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. The composition of the present invention can be prepared by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the s mixed herbal medicine with one or more suitable excipients such as starch, calcium carbonate, sucrose or lactose, gelatin, etc. Except for the simple excipients, lubricants, for example magnesium stearate, talc, etc., can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The preferred dosage of the composition of the present invention varies depending on the condition and weight of a patient, the severity of a disease, the drug form, the route of administration, and the duration, but can be appropriately determined by those skilled in the art. However, for a desirable effect, the composition can be preferably administered at 0.0001 to 1 g/kg per day, and more preferably at 0.001 to 200 mg/kg, but not always limited thereto. The administration frequency can be once a day or a few times a day. The above dosage cannot limit the scope of the invention in any way.

The present invention also provides a health functional food comprising the soybean leaves having a high content of an isoflavone derivative prepared by treating with ethylene, an extract of the soybean leaves, or a fraction of the extract as an active ingredient for the prevention and amelioration of a disease caused by estrogen deficiency.

The disease caused by estrogen deficiency is preferably any one disease selected from the group consisting of osteoporosis, heart disease, breast cancer, vulvar disease, hyperlipidemia, skin aging, and hot flushes, but not always limited thereto.

The physiological activity of the isoflavone derivatives isolated from the soybean leaves having a high content of isoflavones of the present invention has been well established. Therefore, the extract of soybean leaves and its fractions containing the above compounds can be effectively used as a health functional food for the prevention and amelioration of a disease caused by estrogen deficiency.

The health functional food of the present invention can be used by adding the soybean leaves having a high content of an isoflavone derivative, an extract of the soybean leaves, or a fraction of the extract as it is, or can be used together with other foods or food ingredients, and can be appropriately used according to the conventional method.

In this description, "health functional food" indicates the food produced with the supplement of such nutrients that are often lack in daily diet or raw materials or components having a useful function for human body. The health functional food refers to food that helps maintain human health, but not always limited thereto, and is used in the sense of including any general health food.

The form and type of the health functional food are not particularly limited. Specifically, the health functional food can be in the form of tablets, capsules, powders, granules, liquids and pills. The health functional food can additionally include various flavors, sweetening agents or natural carbohydrates. The sweetening agents can be natural sweetening agents such as thaumatin and stevia extract, or synthetic sweetening agents such as saccharin and aspartame. The natural carbohydrates above can be monosaccharides, disaccharides, polysaccharides, oligosaccharides and glucose alcohols.

In addition to the ingredients mentioned above, the health functional food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, etc. All the mentioned ingredients can be added singly or together. The mixing ratio of those ingredients does not matter in fact, but in general, each can be added by 0.01-0.1 weight part per 100 weight part of the composition of the present invention.

The soybean leaves having a high content of an isoflavone derivative of the present invention, the extract of the soybean leaves, or the fraction of the extract can be added to food as it is or used together with other foods or food ingredients. At this time, the content of the added active ingredient can be determined according to the purpose of use. In general, the active ingredient is preferably added to the health functional food by 0.01-90 weight part for the total weight of the food. However, if long term administration is required for health and hygiene or regulating health condition, the content can be lower than the above but higher content can be accepted as well since the active ingredient has been proved to be very safe.

The present invention also provides a pharmaceutical composition for antioxidant, comprising the soybean leaves having a high content of an isoflavone derivative prepared by treating with ethylene in a dark condition, an extract of the soybean leaves, or a fraction of the extract as an active ingredient.

The present invention also provides a health functional food for antioxidant, comprising the soybean leaves having a high content of an isoflavone derivative prepared by treating with ethylene in a dark condition, an extract of the soybean leaves, or a fraction of the extract as an active ingredient.

The physiological activity of the isoflavone derivatives isolated from the soybean leaves having a high content of isoflavones of the present invention has been well established. Therefore, the extract of soybean leaves and its fractions containing the above compounds can be effectively used as an antioxidant composition.

The present invention also provides a pharmaceutical composition for skin care, comprising the soybean leaves having a high content of an isoflavone derivative prepared by treating with ethylene in a dark condition, an extract of the soybean leaves, or a fraction of the extract as an active ingredient.

The present invention also provides a cosmetic composition for skin care, comprising the soybean leaves having a high content of an isoflavone derivative prepared by treating with ethylene in a dark condition, an extract of the soybean leaves, or a fraction of the extract as an active ingredient.

The present invention also provides a health functional food for skin care, comprising the soybean leaves having a high content of an isoflavone derivative prepared by treating with ethylene in a dark condition, an extract of the soybean leaves, or a fraction of the extract as an active ingredient.

The physiological activity of the isoflavone derivatives isolated from the soybean leaves having a high content of isoflavones of the present invention has been well established. Therefore, the extract of soybean leaves and its fractions containing the above compounds can be effectively used as a composition for skin care.

The cosmetic composition can be in the form of lotion, ointment, gel, cream, patch or spray, but not always limited thereto. In the preparation of a cosmetic composition comprising the soybean leaves having a high content of an isoflavone derivative of the present invention, an extract of the soybean leaves, or a fraction of the extract, the soybean leaves having a high content of an isoflavone derivative, the extract of the soybean leaves, or the fraction of the extract can be added to the usually contained composition for external application for skin at 3 to 30 weight part, preferably 5 or 20 weight part.

The cosmetic composition of the present invention can include, in addition to the soybean leaves having a high content of an isoflavone derivative of the present invention, the extract of the soybean leaves, or the fraction of the extract, a supplement generally used in the field of skin science such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturizing agent, essential oil, dye, pigment, hydrophilic or hydrophobic activator, lipid vesicle or other components generally used in cosmetics.

The amount of the above supplement can be determined as generally accepted in the field of skin science.

The present invention also provides a tea using the soybean leaves having a high content of an isoflavone derivative according to the present invention.

The present invention also provides a mixed tea in which the soybean leaves having a high content of an isoflavone derivative according to the present invention and herbal plants having a flavor are mixed.

The tea using the soybean leaves can be manufactured by a preparation method comprising the following steps:
1) washing the soybean leaves having a high content of an isoflavone derivative according to the present invention and then pulverizing;
2) roasting the crushed leaves; and
3) drying the roasted leaves.

In the above method, the pulverizing in step 1) is preferably conducted to a size of 1 to 5 mm using a crusher, but the size is not limited thereto.

In the above method, the roasting in step 2) is preferably conducted at a temperature of 250° C. to 300° C. for 30 to 60 minutes without burning, but the temperature and time are not limited thereto.

In the above method, the drying in step 3) is preferably conducted by natural drying or using a dryer at 30° C. to 50° C. for 24 to 36 hours, but the temperature and time are not limited thereto.

The herbal plant is preferably at least one selected from the group consisting of chamomile, lemongrass, rosehip, lavender, peppermint, fennel, rosemary, jasmine, hibiscus, rose flower, apple fruit, strawberry fruit, lemon fruit and orange flower. And any herb used for tea can be used as the herbal plant. The tea or mixed tea may be processed into a form selected from the group consisting of flavored tea, tea bag, instant tea and can.

Hereinafter, the present invention will be described in detail by the following examples and preparative examples.

However, the following examples and preparative examples are only for illustrating the present invention, and the contents of the present invention are not limited thereto.

Example 1: Preparation of Soybean Leaves Treated with Ethylene in Dark Condition Soybean plants 10 to 15 days after seeding were transplanted into experimental pots, and cultivated for 50 to 60 days until the growth period R1. The cultivated soybean plant pots were placed in a closed space in a dark condition completely blocked from light and stabilized for 24 hours at a temperature of 30° C. and a humidity of 70%. In the closed space under the above conditions, 3000 ppm of ethylene was treated for 6 to 48 hours depending on the growth state of the soybean leaves (the degree of development of the cutin layer). Then, the soybean leaves were obtained immediately after the ethylene treatment and dried at 40° C.

Example 2: Preparation of Ethanol Extract from Soybean Leaves Treated with Ethylene in Dark Condition <2-1> Preparation of Ethanol Extract of Soybean Leaves by Sonication The soybean leaves obtained by the method of <Example 1> were dried, and 50 ml of 90% ethanol was added to 1 g of the dried soybean leaves, followed by extraction at 40° C. while sonication. The extracted solvent was concentrated under reduced pressure to obtain an ethanol extract of soybean leaves in a yield of 15-20%.

<2-2> Preparation of Ethanol Extract of Soybean Leaves at Room Temperature

The soybean leaves obtained by the method of <Example 1> were dried, and 50 ml of 90% ethanol was added to 1 g of the dried soybean leaves, followed by extraction at 25° C. for 5 days. The extracted solvent was concentrated under reduced pressure to obtain an ethanol extract of soybean leaves in a yield of 18-22%.

Example 3: Preparation of Hot Water Extract from Soybean Leaves Treated with Ethylene in Dark Condition The soybean leaves obtained by the method of <Example 1> were dried, and 50 ml of water was added to 1 g of the dried soybean leaves, followed by extraction with hot water at 100° C. for 24 hours. The extracted solvent was concentrated under reduced pressure to obtain a hot water extract of soybean leaves in a yield of 20-25%.

<Experimental Example 1> Confirmation of Accumulation of Isoflavone Derivatives in Ethanol and Hot Water Extracts of Soybean Leaves Treated with Ethylene in Dark Condition HPLC analysis was performed with the extracts prepared in <Example 2-1> and <Example 3> to confirm the accumulation of isoflavone derivatives in the soybean leaves treated with ethylene in a dark condition.

For HPLC, 1290 Infinity LC from Agilent Technologies (Agilent, USA) was used, and ODS-based Zolbox Bonus-RP (150×4.6 mm) was used for the column. The elution rate was 1 ml/min, and a mixed solution of 0.1% aqueous acetic acid (solvent A) and acetonitrile (solvent B) was used as the elution condition. Acetonitrile (solvent B) was applied by gradient elution as shown in Table 1 to separate isoflavone derivatives. At this time, analysis was performed at a detection wavelength of 254 nm.

Figure 2:
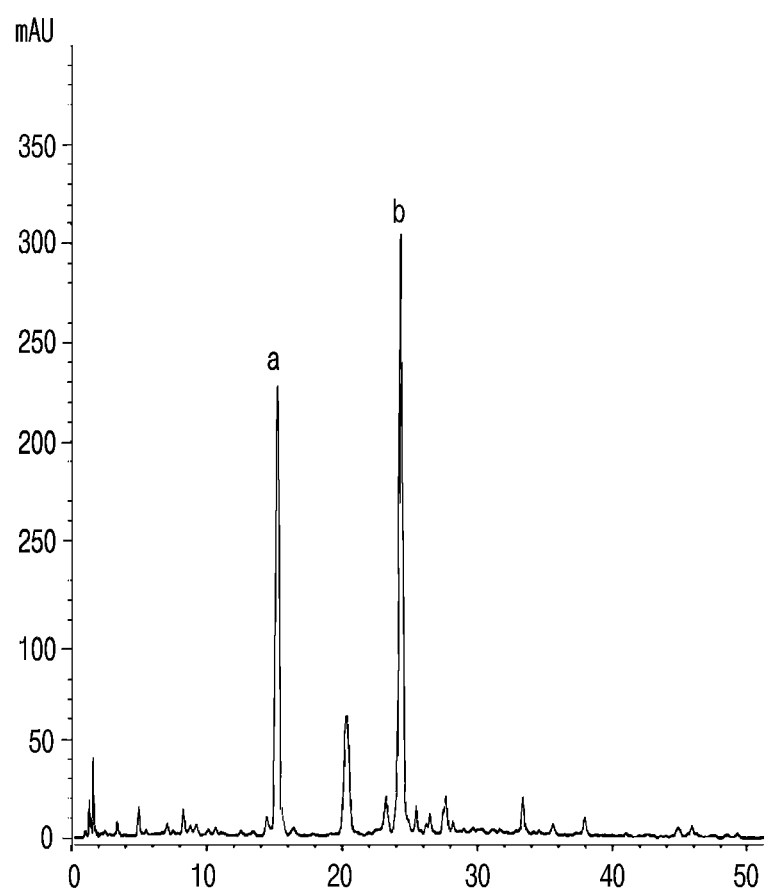
FIG. 2 is a graph showing the HPLC chromatogram (detection wavelength: 254 nm) of the ethanol extract of soybean leaves obtained by treating ethylene in a dark condition (peak a: daidzin, peak b: genistin, peak c: malonyl daidzin, and peak d: malonyl genistin).
Figure 3:
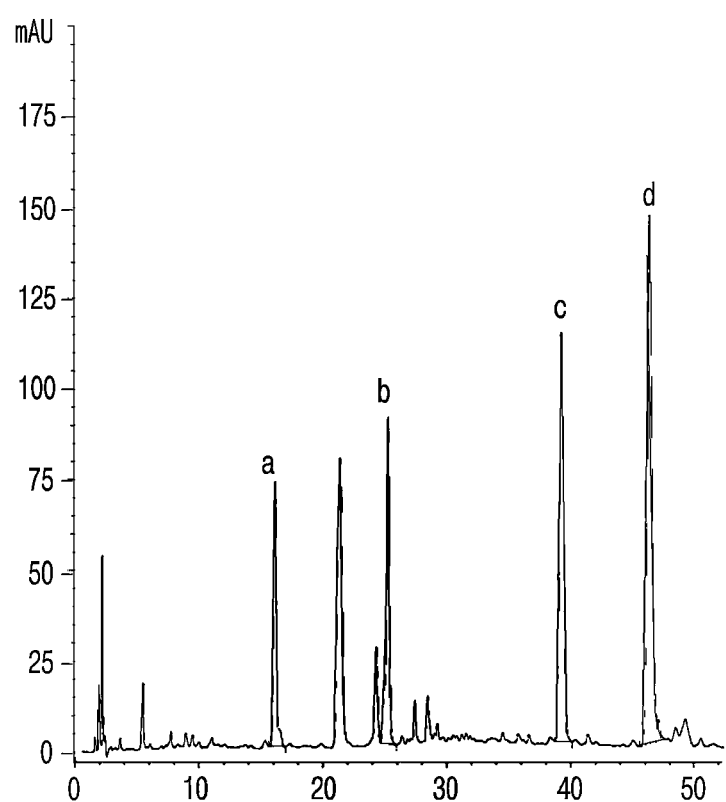
FIG. 3 is a graph showing the HPLC chromatogram (detection wavelength: 254 nm) of the hot water extract of soybean leaves obtained by treating ethylene in a dark condition (peak a: daidzin, and peak b: genistin).

As a result, even in a dark condition, kaempferol glycoside was mainly identified as a metabolite in the soybean leaves not treated with ethylene (FIG. 1), and isoflavone derivatives were rapidly accumulated as shown in FIGS. 2 and 3 when ethylene was treated. Specifically, daidzin (peak a), genistin (peak b), malonyl daidzin (peak c) and malonyl genistin (peak d) were detected at high concentrations in the ethanol extract of soybean leaves treated with ethylene in a dark condition. In the hot water extract of soybean leaves treated with ethylene, it was confirmed that malonyl daidzin (peak c) and malonyl genistin (peak d) were hydrolyzed to daidzin (peak a) and genistin (peak b) (FIGS. 2 and 3). The above results suggest that soybean leaves containing a high content of an isoflavone derivative can be obtained by treating soybean plants with ethylene in a dark condition.

TABLE 1

| Time (min.) | Conc. of solvent B (%) |
|---|---|
| 0-5 | 15% |
| 5-20 | 20% |
| 20-50 | 50% |

<Experimental Example 2> Isolation of Isoflavone Derivatives from Ethylene Extract of Soybean Leaves Obtained by Treating with Ethylene in Dark Condition, Purification and Structural Analysis UPLC-ESI-TOF/MS analysis was performed on the isoflavone derivatives contained in the ethanol extract of Example <2-1>.

Specifically, UPLC BEH C18 column (2.1 mm×100 mm, 1.7 µwaters) was used, and a mixed solution of 0.1% formic acid aqueous solution (solvent A) and 0.1% formic acid acetonitrile (solvent B) was used as the elution condition. Acetonitrile (solvent B) was applied by gradient elution as shown in Table 2 to separate isoflavone derivatives. At this time, the amount of the injected extraction solution was 1 µl, and UPLC-ESI-TOF mass spectrometry was performed under the conditions shown in Table 3.

TABLE 2

| Time (min.) | Conc. of solvent B (%) |
|---|---|
| 0-1 | 3% |
| 1-5 | 15% |
| 5-10 | 25% |
| 10-11 | 30% |
| 11-12 | 45% |

TABLE 3

| Details | Conditions |
|---|---|
| Ionization | ESI-positive mode |
| Capillary voltage | 3 kV |
| Sample cone voltage | 40 V |
| Desolvation gas flow | 800 L/h |
| Cone gas flow | 30 L/h |
| Desolvation temperature | 400° C. |
| Ion source temperature | 100° C. |
| Data collection | m/z 50-1500 rage with a scan time of 0.2 s |
| Lock mass | Leucine-enkephalin (556.2771 Da) |

Figure 4:
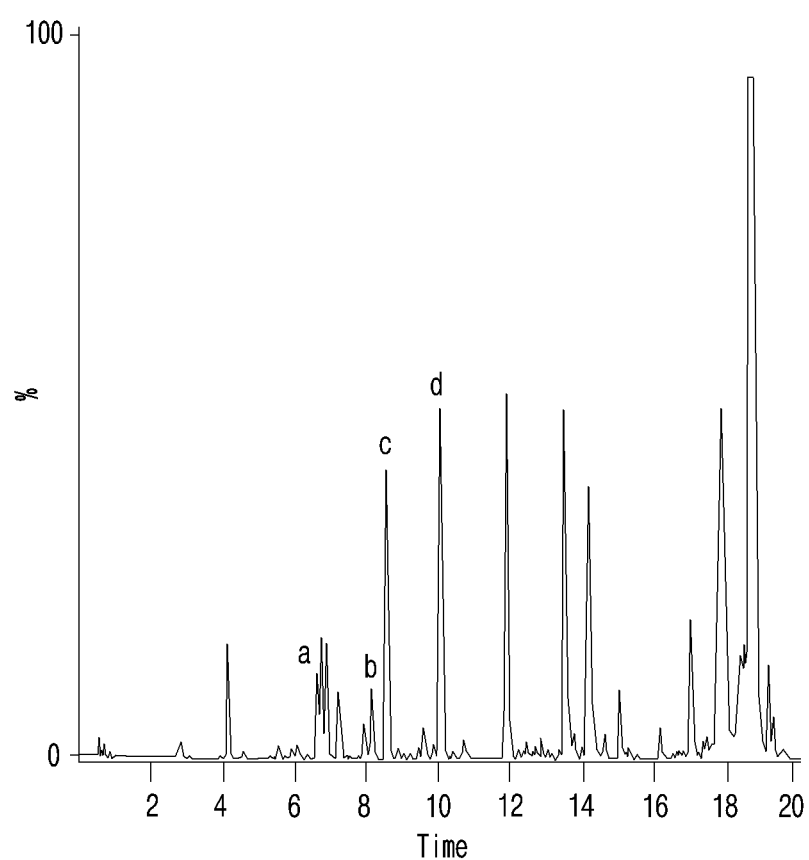
FIG. 4 is a graph showing the LC-ESI-TOF/MS BPI (Base Peak Intensity) chromatogram of the ethanol extract of soybean leaves obtained by treating ethylene in a dark condition (peak a: daidzin, peak b: genistin, peak c: malonyl daidzin, and peak d: malonyl genistin).

As a result, as shown in FIG. 4, BPI (Base Peak Intensity) chromatograms of four isoflavone derivatives were obtained.

Figure 5:
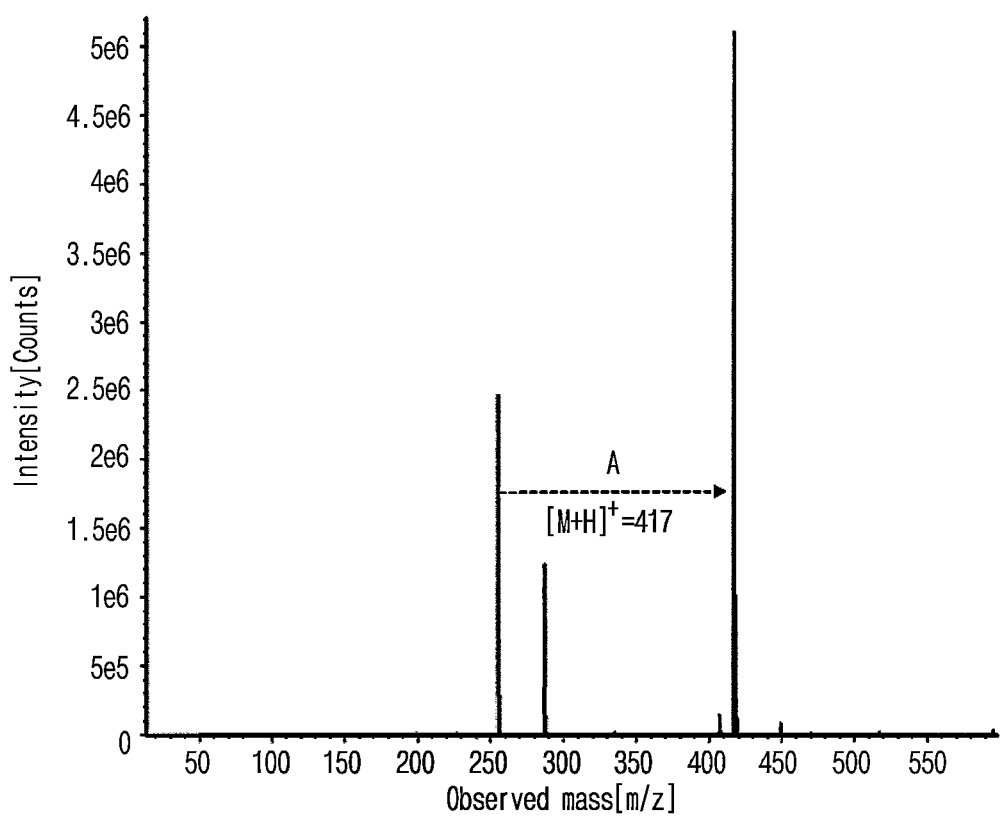
FIG. 5 is a graph showing the high-resolution mass spectrometry (HRESIMS) spectrum of the peak a of FIG. 4 (LC-ESI-TOF/MS BPI).

$[M+H]^+$ was found to be 417.1184 (theoretical value, 417.1186) in the high resolution mass spectrometry (HRESIMS) spectrum of the peak a in FIG. 4. From this, it was confirmed that the elemental composition was $C_{21}H_{21}O_9$, which was consistent with that of daidzin. In addition, the fragment ion 255.0652 [M+H−248] was generated by the detachment of a glucosyl group from daidzin, and the peak a was identified as daidzin since it was consistent with daidzin shown in a reference (J. Agric. Food Chem. 2016, 64, 7315-7324) (FIG. 5).

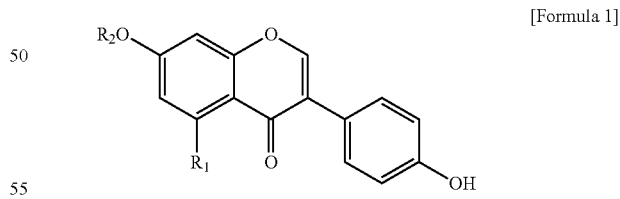

[Formula 1]

Figure 6:
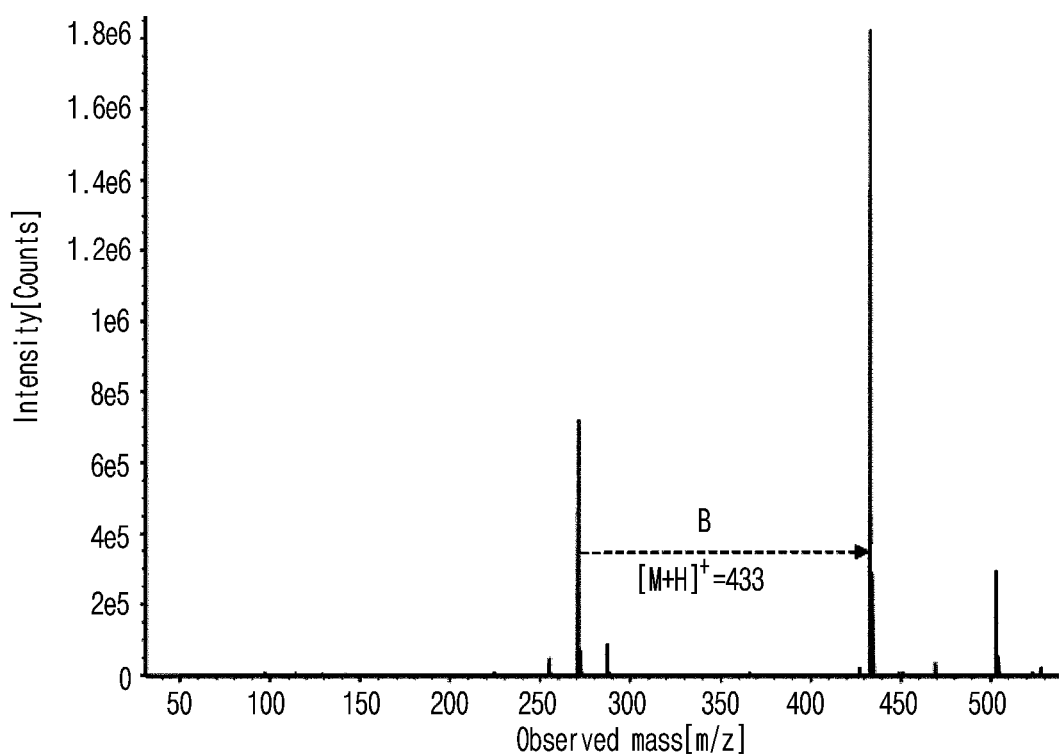
FIG. 6 is a graph showing the high-resolution mass spectrometry (HRESIMS) spectrum of the peak b of FIG. 4 (LC-ESI-TOF/MS BPI).

In addition, $[M+H]^+$ was found to be 433.1133 (theoretical value, 433.1135) in the high resolution mass spectrometry (HRESIMS) spectrum of the peak b in FIG. 4. From this, it was confirmed that the elemental composition was $C_2H_{21}O_{10}$, which was consistent with that of genistin. In addition, the fragment ion 271.0602 [M+H−248] was generated by the detachment of a glucosyl group from genistin, and the peak b was identified as genistin since it was consistent with genistin shown in a reference (J. Agric. Food Chem. 2016, 64, 7315-7324) (FIG. 6).

[Formula 2]

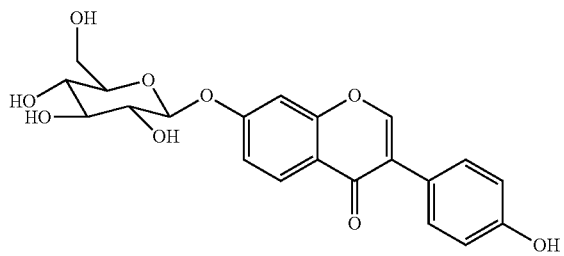

Figure 7:
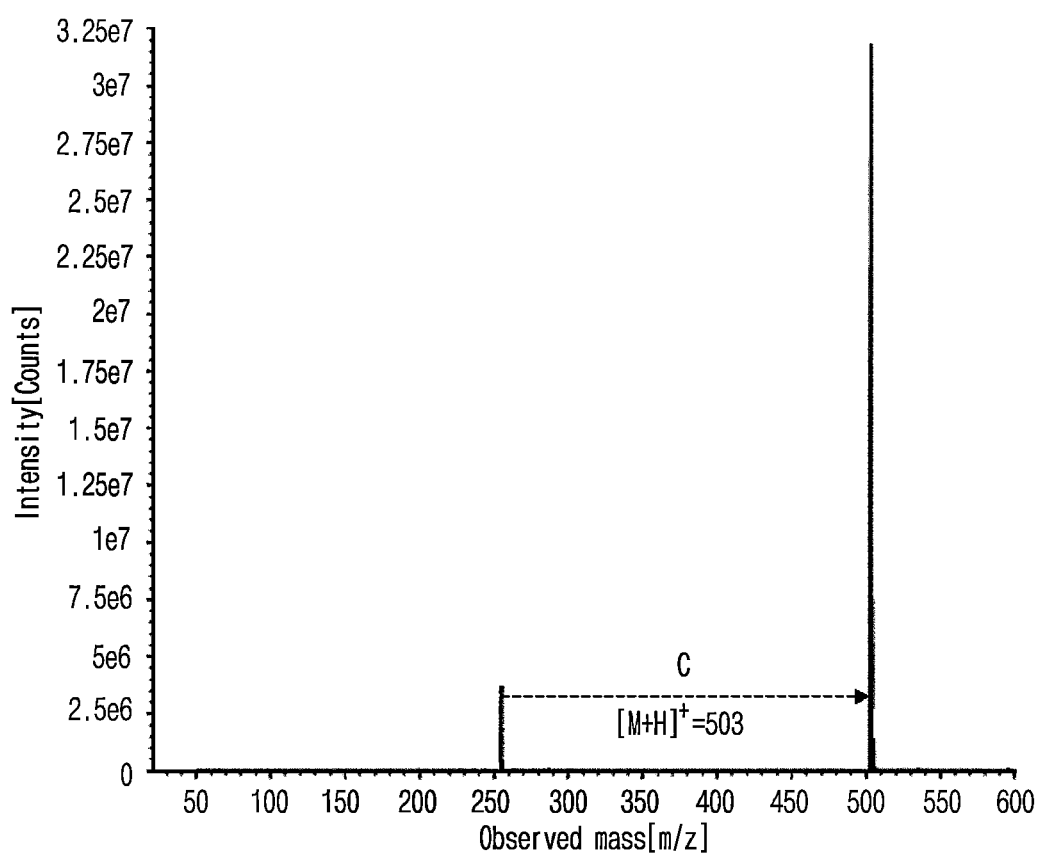
FIG. 7 is a graph showing the high-resolution mass spectrometry (HRESIMS) spectrum of the peak c of FIG. 4 (LC-ESI-TOF/MS BPI).

In addition, [M+H]$^+$ was found to be 503.1195 (theoretical value, 503.1190) in the high resolution mass spectrometry (HRESIMS) spectrum of the peak c in FIG. 4. From this, it was confirmed that the elemental composition was $C_{24}H_{23}O_{12}$, which was consistent with that of malonyl daidzin. In addition, the fragment ion 255.0653 [M+H−248] was generated by the detachment of a malonyl glucosyl group from malonyl daidzin, and the peak c was identified as malonyl daidzin since it was consistent with malonyl daidzin shown in a reference (J. Agric. Food Chem. 2016, 64, 7315-7324) (FIG. 7).

[Formula 3]

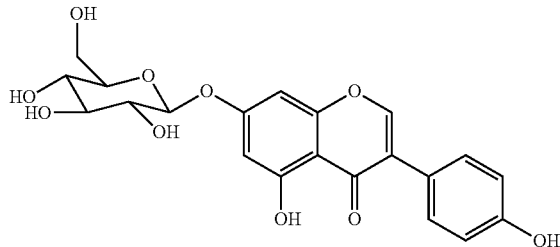

Figure 8:
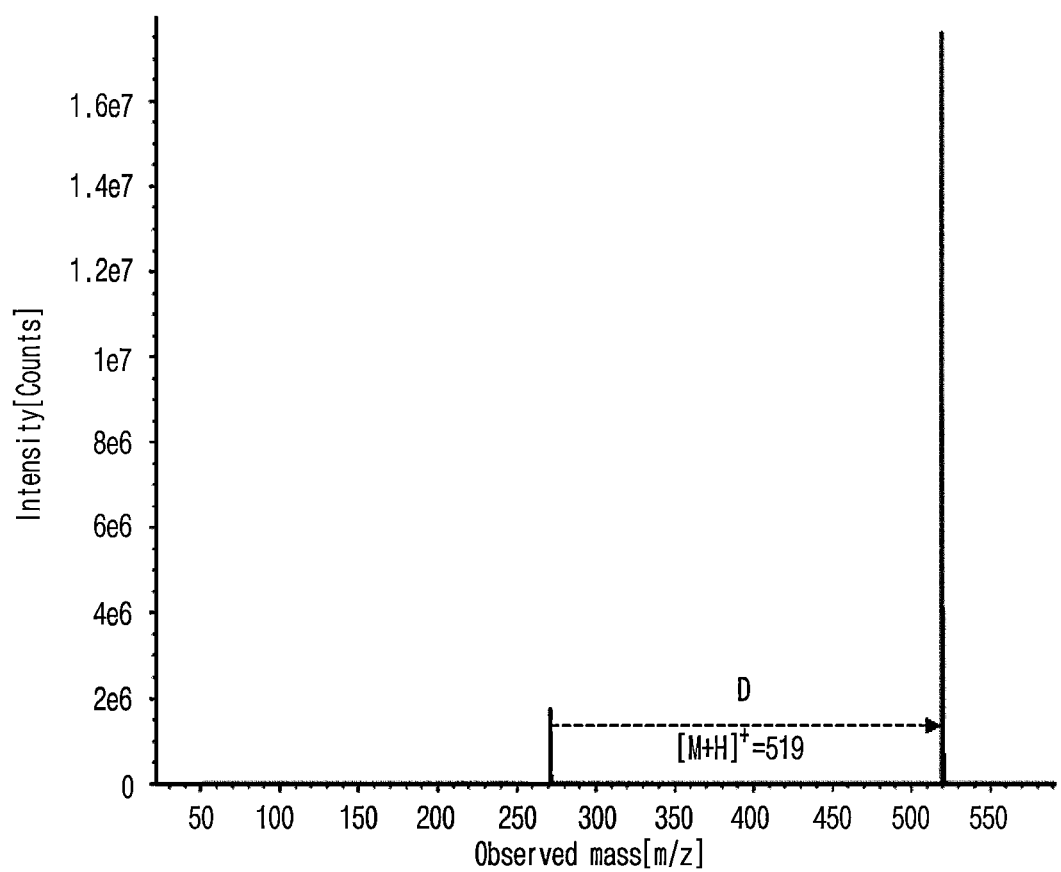
FIG. 8 is a graph showing the high-resolution mass spectrometry (HRESIMS) spectrum of the peak d of FIG. 4 (LC-ESI-TOF/MS BPI).

In addition, [M+H]$^+$ was found to be 519.1141 (theoretical value, 519.1139) in the high resolution mass spectrometry (HRESIMS) spectrum of the peak d in FIG. 4. From this, it was confirmed that the elemental composition was $C_{24}H_{23}O_{13}$, which was consistent with that of malonyl genistin. In addition, the fragment ion 271.0604 [M+H−248] was generated by the detachment of a malonyl glucosyl group from malonyl genistin, and the peak d was identified as malonyl genistin since it was consistent with malonyl genistin shown in a reference (J. Agric. Food Chem. 2016, 64, 7315-7324) (FIG. 8).

[Formula 4]

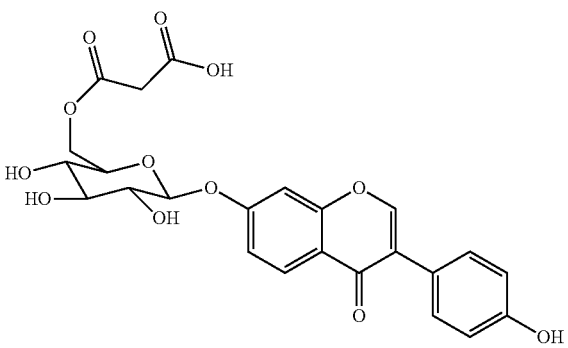

<Experimental Example 3> Quantitative Analysis of Isoflavone Derivatives Using HPLC The ethanol extract of Example 2-1 was filtered using a membrane filtration filter having a pore size of 0.2 μm, and then the total isoflavone amount according to the presence or absence of ethylene treatment, treatment concentration and time was measured.

Specifically, 1290 Infinity LC of Agilent Technologies (Agilent, USA) was used for HPLC, and ODS series Zolbox Bonus-RP (150×4.6 mm) was used for the column. As mobile phases, 0.1% aqueous acetic acid solution (solvent A) and acetonitrile (solvent B) were used, and the gradient elution shown in Table 4 was applied. The flow rate was adjusted to 1 ml/min, the amount of the injected extraction solution was 10 μl, and the detection wavelength was 254 nm. The standard solution used for quantitative analysis was prepared in the range of 1-100 μg/ml by dissolving 98% pure daidzin and genistin purchased from Sigma (USA) in methanol. HPLC analysis was performed with the prepared standard solution, and a calibration curve was prepared from the peak area. At this time, the retention times (RT) of daidzin and genistin were 13.19 minutes and 23.89 minutes, respectively.

As a result, when ethylene was treated with various concentrations at a temperature of 30±5° C. for 24 hours in a dark condition, the total amount of isoflavone showed the highest value of 26500 μg/g at 3000 ppm, confirming that 3000 ppm was the optimal concentration of ethylene (Table 5).

In addition, ethylene was treated at a concentration of 3000 ppm at 30±5° C. for 6 to 48 hours in a dark condition. As a result, the total amount of isoflavone showed the highest value of 26500 μg/g when treated for 24 hours, confirming that 24 hours was the optimal treatment time (Table 6).

TABLE 4

| Time (min.) | Conc. of solvent B (%) |
|---|---|
| 0-5 | 15% |
| 5-20 | 20% |
| 20-50 | 50% |

TABLE 5

| Isoflavone | Conc. of ethylene (ppm) | | | |
|---|---|---|---|---|
| (μg) | 500 | 1000 | 2000 | 3000 |
| Daidzin | 476 | 1024 | 1923 | 2754 |
| Genistin | 938 | 2016 | 3787 | 5424 |
| Malonyl daidzin | 1298 | 2792 | 5245 | 7513 |
| Malonyl genistin | 2506 | 5390 | 10124 | 14502 |
| Total | 4580 | 9850 | 18500 | 26500 |

TABLE 6

| Isoflavone | Treatment time (hr) | | | |
|---|---|---|---|---|
| (μg) | 6 | 12 | 24 | 48 |
| Daidzin | 996 | 1964 | 2754 | 2557 |
| Genistin | 1961 | 3869 | 5424 | 5036 |

TABLE 6-continued

| Isoflavone (μg) | Treatment time (hr) | | | |
|---|---|---|---|---|
| | 6 | 12 | 24 | 48 |
| Malonyl daidzin | 2716 | 5358 | 7513 | 6974 |
| Malonyl genistin | 5243 | 10343 | 14502 | 13462 |
| Total | 9580 | 18900 | 26500 | 24600 |

<Experimental Example 4> Comparative Analysis of Isoflavone Derivative Content in Case of Ethylene Treatment in Dark Condition and Ethephon Treatment in Light Condition An experiment comparing the content of isoflavone derivatives between the soybean leaves having a high content of an isoflavone derivative prepared by treating ethephon in a light condition and the soybean leaves having a high content of an isoflavone derivative prepared by treating ethylene in a dark condition of the present invention was performed as follows.

Specifically, 50 soybean plant pots for each experiment group were prepared in the same manner and conditions as in Example 1. Soybean leaves were obtained immediately after treating 800 ppm of ethephon to the soybean plant pots cultivated in a light condition at a temperature of 28±10° C. for 96 hours, and then dried thereof at 40° C. The cultivated soybean plant pots were placed in a closed space in a dark condition completely blocked from light and stabilized for 24 hours at a temperature of 30° C. and a humidity of 60%, and then 3000 ppm of ethylene was treated for 24 hours. Immediately after the treatment, soybean leaves were obtained and dried at 40° C. The obtained dried soybean leaves were treated under the same conditions and methods as in Experimental Example 3 to prepare an ethanol extract of soybean leaves, and quantitative analysis was performed on the content of isoflavone derivatives.

Figure 9:
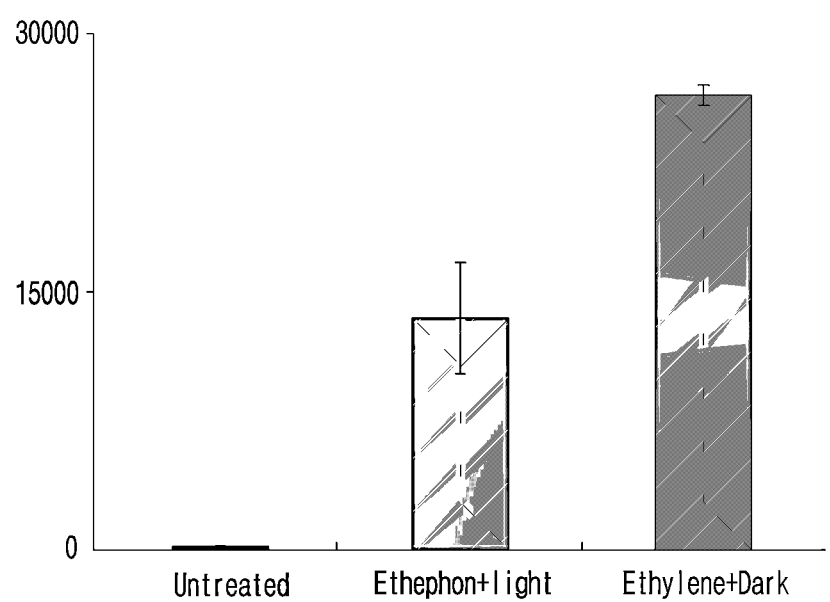
FIG. 9 is a graph showing the results of comparing the total isoflavone content of soybean leaves not treated with ethylene, soybean leaves treated with ethephon in a light condition, and soybean leaves treated with ethylene in a dark condition.

As a result, as shown in Table 7 and FIG. 9, the soybean leaves treated with 800 ppm of ethephon in a light condition contained 13500 μg/g of isoflavone derivatives, whereas the soybean leaves treated with 3000 ppm of ethylene in a dark condition contained 26500 μg/g of total isoflavone derivatives. Therefore, it was confirmed that the content of isoflavone derivatives was increased by about two times when ethylene was treated in a dark condition. In addition, it was confirmed that the standard deviation of the average value of the isoflavone derivative content was reduced to ¼ when ethylene was treated in a dark condition, so that the homogeneity of the standard deviation was improved. The above results indicate that when ethylene is treated at the optimum concentration in a dark condition, the content of isoflavone derivatives is significantly increased, and soybean leaves having a high content of an isoflavone derivative can be stably obtained.

TABLE 7

| | Non-treated soybean leaves | Soybean leaves treated with ethephon in light condition | Soybean leaves treated with ethylene in dark condition |
|---|---|---|---|
| Total isoflavone content (μg) | <200 | 13500 ± 02500 | 26500 ± 0600 |

The Manufacturing Examples of the composition for the present invention are described hereinafter.

Manufacturing Example 1: Preparation of Pharmaceutical Formulations

<1-1> Preparation of Powders

The soybean leaves having a high content of an isoflavone derivative of the present invention, an extract of the soybean leaves or a fraction of the

| extract | 0.1 g |
|---|---|
| Lactose | 1.5 g |
| Talc | 0.5 g |

Powders were prepared by mixing all the above components, which were filled in airtight packs according to the conventional method for preparing powders.

<1-2> Preparation of Tablets

The soybean leaves having a high content of an isoflavone derivative of the present invention, an extract of the soybean leaves or a fraction of the

| extract | 0.1 g |
|---|---|
| Lactose | 7.9 g |
| Crystalline cellulose | 1.5 g |
| Magnesium stearate | 0.5 g |

After mixing the above ingredients, tablets were prepared by direct tableting method.

<1-3> Preparation of Capsules

The soybean leaves having a high content of an isoflavone derivative of the present invention, an extract of the soybean leaves or a fraction of the

| extract | 0.1 g |
|---|---|
| Corn starch | 5 g |
| Carboxy cellulose | 4.9 g |

Powders were prepared by mixing all the above components, and the powders were filled in hard capsules to prepare capsules according to the conventional method for preparing capsules.

<1-4> Preparation of Injectable Solutions

The soybean leaves having a high content of an isoflavone derivative of the present invention, an extract of the soybean leaves or a fraction of the

| extract | 0.1 g |
|---|---|
| Sterile distilled water for injection | proper amount |
| pH regulator | proper amount |

Injectable solutions were prepared by mixing all the above components, putting the mixture into 2 ml ampoules by the conventional method for preparing injectable solutions.

<1-5> Preparation of Liquid Formulations

The soybean leaves having a high content of an isoflavone derivative of the present invention, an extract of the soybean leaves or a fraction of the

| | |
|---|---|
| extract | 0.1 g |
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

Manufacturing Example 2: Preparation of Health Food

<2-1> Preparation of Powders

A mixed tea was prepared by mixing the soybean leaves having a high content of an isoflavone derivative of the present invention, an extract of the soybean leaves or a fraction of the extract and an herbal plant having flavor.

<2-2> Preparation of Flour Food 0.5 to 5.0 weight part of the soybean leaves having a high content of an isoflavone derivative of the present invention, an extract of the soybean leaves or a fraction of the extract was added to wheat flour, and the mixture was used to prepare breads, cakes, cookies, crackers and noodles.

<2-3> Preparation of Soups and Gravies 0.1 to 5.0 weight part of the soybean leaves having a high content of an isoflavone derivative of the present invention, an extract of the soybean leaves or a fraction of the extract was added to soups and gravies. Health enhancing meat products, soups and gravies were prepared with this mixture by the conventional method.

<2-4> Preparation of Ground Beef

Health enhancing ground beef was prepared by mixing weight part of the soybean leaves having a high content of an isoflavone derivative of the present invention, an extract of the soybean leaves or a fraction of the extract with ground beef according to the conventional method.

<2-5> Preparation of Dairy Products 5 to 10 weight part of the soybean leaves having a high content of an isoflavone derivative of the present invention, an extract of the soybean leaves or a fraction of the extract was added to milk. Health enhancing dairy products such as butter and ice cream were prepared with the milk mixture according to the conventional method.

<2-6> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The soybean leaves having a high content of an isoflavone derivative of the present invention, an extract of the soybean leaves or a fraction of the extract was concentrated under reduced pressure, spray-dried and pulverized to obtain 60-mesh dry powders.

Sun-Sik was prepared by mixing the dry powders of the grains, seeds and the soybean leaves having a high content of an isoflavone derivative of the present invention, an extract of the soybean leaves or a fraction of the extract according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), Dry powders of the soybean leaves having a high content of an isoflavone derivative of the present invention, an extract of the soybean leaves or a fraction of the extract (3 weight part),

*Ganoderma lucidum* (0.5 weight part),
*Rehmannia glutinosa* (0.5 weight part)

Manufacturing Example 3: Preparation of Health Beverages

The soybean leaves having a high content of an isoflavone derivative of the present invention, an extract of the soybean leaves or a fraction of the

| | |
|---|---|
| extract | 100 mg |
| Citric acid | 100 mg |
| Oligosaccharide | 100 mg |
| Maesil (*Prunus mume*) extract | 2 mg |
| Taurine | 100 mg |
| Purified water | up to 500 ml |

The above constituents were mixed according to the conventional method for preparing health beverages. The mixture was heated at 85° C. for 1 hour with stirring and then filtered. The filtrate was loaded in 1 ℓ sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted to regional and ethnic preferences such as the demanding class, the demanding country, and the purpose of use.

Manufacturing Example 4: Preparation of Cosmetic Composition

<4-1> Preparation of Cream

The soybean leaves having a high content of an isoflavone derivative of the present invention, an extract of the soybean leaves or a fraction of the

| | |
|---|---|
| extract | 4.6 weight part |
| Cetostearyl alcohol | 2.8 weight part |
| Beeswax | 2.6 weight part |
| Stearic acid | 1.4 weight part |
| Glyceryl monostearate, lipophilic | 2 weight part |
| PEG-100 stearate | 1 weight part |
| Sorbitan sesquioleate | 1.4 weight part |
| Jojoba oil | 4 weight part |
| Squalene | 3.8 weight part |
| Polysorbate | 1.1 weight part |
| Macadamia oil | 2 weight part |
| Tocopherol acetate | 0.2 weight part |
| Methylpolysiloxane | 0.4 weight part |

-continued

| | |
|---|---|
| Ethyl paraben | 0.1 weight part |
| Propyl paraben | 0.1 weight part |
| Euxyl K-400 | 0.1 weight part |
| 1,3-Butyleneglycol | 7 weight part |
| Methyl paraben | 0.05 weight part |
| Glycerine | 6 weight part |
| D-panthenol | 0.2 weight part |
| Triethanolamine | 0.2 weight part |
| pt 41891 | 0.2 weight part |
| p-H2O | 46.05 weight part |

<4-2> Preparation of Cream

The soybean leaves having a high content of an isoflavone derivative of the present invention, an extract of the soybean leaves or a fraction of the

| | |
|---|---|
| extract | 3.5 weight part |
| Cetostearyl alcohol | 1.6 weight part |
| Stearic acid | 1.4 weight part |
| Glyceryl monostearate, lipophilic | 1.8 weight part |
| PEG-100 stearate | 2.6 weight part |
| Sorbitan sesquioleate | 0.6 weight part |
| Squalene | 4.8 weight part |
| Macadamia oil | 2 weight part |
| Jojoba oil | 2 weight part |
| Tocopherol acetate | 0.4 weight part |
| Methylpolysiloxane | 0.2 weight part |
| Ethyl paraben | 0.1 weight part |
| Propyl paraben | 0.1 weight part |
| 1,3-Butyleneglycol | 4 weight part |

-continued

| | |
|---|---|
| Methyl paraben | 0.1 weight part |
| Xanthan gum | 0.1 weight part |
| Glycerine | 4 weight part |
| D-panthenol | 0.15 weight part |
| Allantoin | 0.1 weight part |
| Carbomer (2% aq. Sol) | 4 weight part |
| Triethanolamine | 0.15 weight part |
| Ethanol | 3 weight part |
| pt 41891 | 0.1 weight part |
| p-H2O | 48.3 weight part |

What is claimed is:

1. A method of preparing soybean leaves containing an isoflavone derivative content of 18,900 micrograms-27,100 micrograms of the isoflavone derivative per gram of the soybean leaves comprising:
  a) stabilizing a soybean plant by placing the soybean plant for 40 days to 60 days after seeding of the soybean plant in a closed space under dark conditions where light is blocked for 20 hours to 30 hours; and
  b) treating the soybean plant in the closed space under dark conditions with ethylene at a concentration of 2500 ppm to 3500 ppm of ethylene in air for 6 hours to 48 hours after completing step a) so as to stimulate production of the isoflavone derivative in the soybean leaves to yield soybean leaves containing an isoflavone derivative content of 18,900 micrograms-27,100 micrograms of the isoflavone derivative per gram of the soybean leaves.

* * * * *